(12) United States Patent
Potok et al.

(10) Patent No.: US 10,643,031 B2
(45) Date of Patent: May 5, 2020

(54) SYSTEM AND METHOD OF CONTENT BASED RECOMMENDATION USING HYPERNYM EXPANSION

(71) Applicant: UT-Battelle, LLC, Oak Ridge, TN (US)

(72) Inventors: Thomas E. Potok, Oak Ridge, TN (US); Robert M. Patton, Knoxville, TN (US); Sreenivas R. Sukumar, Oak Ridge, TN (US)

(73) Assignee: UT-Battelle, LLC, Oak Ridge, TN (US)

(*) Notice: Subject to any disclaimer, the term of this patent is extended or adjusted under 35 U.S.C. 154(b) by 206 days.

(21) Appl. No.: 15/455,260

(22) Filed: Mar. 10, 2017

(65) Prior Publication Data

US 2017/0262528 A1    Sep. 14, 2017

Related U.S. Application Data

(60) Provisional application No. 62/306,662, filed on Mar. 11, 2016.

(51) Int. Cl.
*G06F 40/30* (2020.01)
*G06F 16/33* (2019.01)
(Continued)

(52) U.S. Cl.
CPC .......... *G06F 40/30* (2020.01); *G06F 16/3338* (2019.01); *G06F 16/3347* (2019.01); *G06F 19/30* (2013.01); *G06F 40/242* (2020.01)

(58) Field of Classification Search
CPC ............ G06F 17/2735; G06F 17/2785; G06F 17/30672; G06F 17/3069; G06F 19/00;
(Continued)

(56) References Cited

U.S. PATENT DOCUMENTS

| 5,950,189 A | 9/1999 | Cohen et al. |
| 6,542,889 B1 | 4/2003 | Aggarwal et al. |

(Continued)

FOREIGN PATENT DOCUMENTS

| WO | 2010/014082 | 2/2010 |
| WO | 2011/099982 | 8/2011 |

OTHER PUBLICATIONS

Gaussier, E. et al., "A Geometric View on Bilingual Lexicon Extraction from Comparable Corpora," Proceedings of the 42nd Annual Meeting of the Association for Computational Linguistics, pp. 527-534.
(Continued)

*Primary Examiner* — Irete F Ehichioya
*Assistant Examiner* — Xiaoqin Hu
(74) *Attorney, Agent, or Firm* — Warner Norcross + Judd LLP (57) ABSTRACT

A system and method for document recommendation combines linguistic and term frequency approaches in order to improve overall performance and recommendation. Hypernyms are added to the source document set so that related documents can be recommended from the source document set. There are a variety of different parameters to configure that change operation of the document recommendation system.

19 Claims, 3 Drawing Sheets

(51) Int. Cl.
*G06F 40/242* (2020.01)
*G06F 19/00* (2018.01)

(58) Field of Classification Search
CPC .. G06F 19/30; G06F 16/3338; G06F 16/3347; G06F 40/242; G06F 40/30; G16H 70/00
USPC .................................................. 707/600–899
See application file for complete search history.

(56) References Cited

U.S. PATENT DOCUMENTS

| | | | |
|---|---|---|---|
| 6,990,628 B1 | 1/2006 | Palmer et al. | |
| 7,225,183 B2 | 5/2007 | Gardner | |
| 7,693,903 B2 | 4/2010 | Potok et al. | |
| 7,805,446 B2 | 9/2010 | Potok et al. | |
| 7,844,566 B2 | 11/2010 | Wnek | |
| 7,937,389 B2 | 5/2011 | Jiao et al. | |
| 7,958,136 B1 | 6/2011 | Curtis et al. | |
| 9,256,649 B2 | 2/2016 | Patton et al. | |
| 9,558,185 B2 | 1/2017 | Potok et al. | |
| 2003/0154071 A1 | 8/2003 | Shreve | |
| 2004/0029085 A1* | 2/2004 | Hu | G06F 17/2745 434/178 |
| 2007/0073533 A1* | 3/2007 | Thione | G06F 17/279 704/9 |
| 2007/0130100 A1 | 6/2007 | Miller | |
| 2007/0185871 A1 | 8/2007 | Canright et al. | |
| 2009/0070325 A1 | 3/2009 | Gabriel et al. | |
| 2009/0089047 A1* | 4/2009 | Pell | G06F 17/2785 704/9 |
| 2009/0132566 A1 | 5/2009 | Ochi et al. | |
| 2011/0196870 A1 | 8/2011 | Schmidtler et al. | |
| 2013/0339373 A1* | 12/2013 | Patton | G06F 17/3053 707/749 |
| 2014/0337337 A1 | 11/2014 | Chen et al. | |
| 2016/0224637 A1 | 8/2016 | Sukumar et al. | |
| 2017/0228599 A1* | 8/2017 | De Juan | G06K 9/00697 |
| 2018/0336902 A1* | 11/2018 | Cartwright | G06F 17/2785 |

OTHER PUBLICATIONS

Strasberg, H. et al., "What's related? Generalizing Approaches to Related Articles in Medicine," in AMIA Symposium, 2000, pp. 838-842.

Reed J.W. et al., "TF-ICF: A New Term Weighting Scheme for Clustering Dynamic Data Streams," Proceedings of the 5th Internationanl Conference on Machine Learning and Applications, Dec. 2006, pp. 1-6.

Adomavicius, G. et al., "Toward the next generation of recommender systems: a survey of the state-of-the-art and possible extensions," Knowledge and Data Engineering, IEEE Transactions on , vol. 17, No. 6, pp. 734,749, Jun. 2005.

Narducci, F. et al., "Exploiting Big Data for Enhanced Representations in Content-Based Recommender Systems", EC-Web 2013: pp. 182-193.

Patton, R. et al., "Discovery & Refinement of Scientific Information via a Recommender System", INFOCOMP 2012, The Second International Conference on Advanced Communications and Computation, pp. 31-35.

* cited by examiner

SYSTEM AND METHOD OF CONTENT BASED RECOMMENDATION USING HYPERNYM EXPANSION

CROSS-REFERENCE TO RELATED APPLICATIONS

This patent application claims the benefit of U.S. Provisional Patent Application Ser. No. 62/306,662 to Potok et al, entitled "A High Performance Content Based Recommender System Using Hypernym Expansion", filed Mar. 11, 2016, which is herein incorporated by reference in its entirety.

This patent application is related to U.S. Pat. No. 9,256,649 to Patton et al., granted on Feb. 9, 2016, entitled "Method and System of Filtering and Recommending Documents", which is herein incorporated by reference in its entirety.

This patent application is related to U.S. Pat. No. 7,805,446 to Potok et al., granted on Sep. 28, 2010, entitled "Agent-based method for distributed clustering of textual information", which is herein incorporated by reference in its entirety.

This patent application is related to U.S. Pat. No. 7,693,903 to Potok et al., granted on Apr. 6, 2010, entitled "Method for gathering and summarizing internet information", which is herein incorporated by reference in its entirety.

This patent application is related to U.S. Pat. No. 7,937,389 to Jiao et al., granted on May 3, 2011, entitled "Dynamic reduction of dimensions of a document vector in a document search and retrieval system", which is herein incorporated by reference in its entirety.

This patent application is related to U.S. Pat. No. 9,558,185 to Potok et al., granted on Jan. 31, 2017, entitled "Method and System to Discover and Recommend Interesting Documents", which is herein incorporated by reference in its entirety.

This patent application is related to U.S. patent application Ser. No. 15/004,402 to Sukumar et al., filed on Jan. 22, 2016, entitled "Processing Associations in Knowledge Graphs", which is herein incorporated by reference in its entirety.

STATEMENT REGARDING FEDERALLY SPONSORED RESEARCH AND DEVELOPMENT

This invention was made with government support under Contract No. DE-AC05-00OR22725 awarded by the U.S. Department of Energy. The government has certain rights in the invention.

BACKGROUND OF THE INVENTION

1. Field of the Invention

The present disclosure relates to computers and more specifically to methods for improving a computer's ability to locate similar documents within a large set of documents.

2. Description of the Related Art

Finding content similarity over large sets of documents is a well-studied area. Two distinct approaches to finding similar documents within a large document set include 1) using semantic information for a document comparison between seed and target documents; and 2) use of a term frequency method to represent documents as mathematical vectors so that seed document vectors and target document vectors can be easily compared.

Use of semantic information typically involves using linguistic methods to analyze document sets and perform comparisons based on the linguistic analysis. Given reasonable training sets and time, these approaches can be effective in determining the similarity of documents. The main drawback with these approaches tends to be performance. These methods are typically computationally expensive, thus limiting the number of documents that can be effectively analyzed. Another challenge is the need for retraining if the domain of the documents shifts or changes.

The second general approach to finding documents with similar content is to use a term frequency method to represent a document as a mathematical vector which can easily be compared to other vectors. There are a wide variety of methods to perform this transformation from documents to vectors, and a wide variety of methods to compare the similarity of the resulting vectors. These term frequency methods are typically faster than linguistic methods, but can easily mislabel documents.

For very large document sets, even term frequency based methods have performance challenges. The widely used term frequency-inverse document frequency (TF/IDF) method requires a count of documents that contain a given term in order to calculate a weight for that term, meaning that the inverse document frequency (how many documents contain a given term), must be calculated for every unique term in the set before a given document vector can be created. This forces process serialization over a set of documents.

The term frequency-inverse corpus frequency (TF/ICF) method addresses the performance challenges of TF/IDF, and results show that it can provide more accurate results on homogenous data sets than does TF/IDF, however, it still retains the weakness of mislabeling similar documents as does TF/IDF or any term frequency based method.

Further improvements can advance the state of the art.

BRIEF SUMMARY OF THE INVENTION

The present invention combines linguistic document recommendation with term frequency document recommendation to provide an improved document recommendation system and method. The system and method includes defining or obtaining a seed document set and a source document set. The seed documents and source documents are vectorized using a term frequency method. Either before or after the seed document set is vectorized, additional terms can be added to each seed document or seed document vector using hypernym expansion. The hypernym expansion may include three steps: determining which terms to expand, discovering one or more hypernyms for each term, and determining which hypernyms to insert into the seed document or seed document vector. Once the expansion is complete for a seed document and that document is in vector form it can be compared to the source document vectors to produce a document recommendation set based on vector similarity. Because the seed document set includes additional terms based on hypernymy, the accuracy and/or quality of the recommendation is increased.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

BRIEF DESCRIPTION OF THE SEVERAL VIEWS OF THE DRAWINGS

A more complete understanding of the preferred embodiments will be more readily understood by reference to the following detailed description when considered in conjunction with the accompanying drawings where like numerals indicate common elements among the various figures.

The system and/or method may be better understood with reference to the following drawings and description. Non-limiting and non-exhaustive descriptions are described with reference to the following drawings. The components in the figures are not necessarily to scale, emphasis instead being placed upon illustrating principles. In the figures, like referenced numerals may refer to like parts throughout the different figures unless otherwise specified.

DETAILED DESCRIPTION OF THE INVENTION

The current embodiment combines linguistic document recommendation with term frequency document recommendation to provide an improved document recommendation system and method. One embodiment of a method of the present invention is described in connection with the flowchart 100 illustrated in FIG. 1. The method includes defining or obtaining a seed document set 102 and a source document set 110. The seed and source documents can be identified by accompanying identifiers, e.g. titles or ID numbers. The seed documents and source documents are processed, which includes converting the documents to vectors 108, 112 using a term frequency method, such as term frequency inverse corpus frequency (TF/ICF) or term frequency inverse document frequency (TF/IDF). Either before or after each seed document in the seed document set is converted to a vector, additional terms can be added to each seed document or seed document vector using semantic relationship expansion 106. Which terms are added to which seed document or seed document vector can vary depending on a variety of factors that can vary from application to application or based on criteria selected by a user. In some embodiments, a parts of speech analysis 104 may facilitate the decision. Once the seed documents and source documents are processed, they can be compared 114 to produce a document recommendation set 116 based on vector similarity. The recommendation set may include copies of the documents, links to the documents, or document identifiers. Because the seed document set includes additional terms based on semantic relationships, the accuracy and/or quality of the recommendation is increased.

In the illustrated embodiment, the semantic relationship expansion is hypernym expansion. A hypernym is a more general term formed by an "is-a" relationship between two words, e.g., a "lesion" is a "tumor", therefore "tumor" is a hypernym of "lesion" and a "beagle" is a "dog", therefore "dog" is a hypernym of "beagle". By including additional hypernymic terms in the seed document set, the accuracy and/or quality of the document recommendation system can be increased.

Other types of semantic relationship expansion can be performed instead of or in addition to hypernym expansion, for example, hyponym expansion. Hyponymy and hypernymy refer to the ship between generic tee (hypernym) and a specific instance (hyponym). A hyponym is a term whose semantic field is more specific than its hypernym, while the semantic field of a hypernym is broader than that of a hyponym. Accordingly, in the example above, "lesion" is a hyponym of "tumor".

To expand on the example above, a technical seed document may use the term "lesion" to represent damaged tissues, while a more general or higher level news article in the source document set may use the term "tumor" to represent the same concept. In this simplistic example, the higher level news article may not be discovered by a conventional term frequency document searching method because the news article does not use the specific term "lesion". However, in the disclosed hybrid semantic/term frequency approach, the article may be found and recommended because the term "tumor" is added to the seed document set by virtue of being a hypernym of "lesion", which occurs in one of the seed documents.

By inserting hypernyms in the seed document set, the seed document can be generalized, which addresses the over-specialization problem seen by many recommender systems. Overspecialization occurs when a very technical document recommends other very technical documents, and not a high level document on the same topic. The current embodiment of the system and method broadens the language used for comparison to recommend more "interesting" documents. To find the appropriate hypernyms takes additional time, so to maintain high performance, in the current embodiment, hypernyms are only added to the seed document set, a much smaller set than the source document set. This reduces the natural language processing (NLP) performance impact. In alternative embodiments, a semantic relationship expansion, such as hypernym expansion, may be conducted on the source document set instead of or in addition to the seed document set.

Referring back to FIG. 1, the input to the system includes one or more seed documents 102, which are a set of documents that contain information that is of significant interest to the user; and a set of source documents 110, which are documents that may contain information of interest to the user. In general, the source documents are contained in a library of documents that may contain up to thousands, tens of thousands, hundreds of thousands, or even millions or more of source documents. It can be appreciated that recommending one or more source documents from a library of a million or more source documents, which are similar to one or more seed documents, is beyond the capability of a human. Thus, a computer device that performs the disclosed method steps is a useful device and is an improvement over conventional computers.

Processing seed and source documents 103, 111 to convert them to vectors allows for their mathematical comparison and determining the similarity between two documents. A document vector is a mathematical representation of the term frequencies of a document. For example, a document vector can be represented by a list of words and the number of times each word appears in the document. Seed documents are the documents of interest upon which a search is performed. Source or target documents are the documents that make up the pool of documents that are being searched. Seed document vectors and source document vectors refer to the document vectors of the seed documents and the document vectors of the target documents, respectively.

Documents can be obtained from essentially any source and the way in which a user obtains documents can vary from application to application. For example, seed documents or source documents can be obtained from the Internet, or another database. In one example, ten publicly available research papers can be used as a set of seed documents, i.e., documents of interest chosen by the user of the system. These seed documents can be downloaded to a local computing machine, converted to text files, and stored on a local computing machine. The documents may be stored in a local or remote database. Although ten seed documents were chosen in this example, additional or fewer documents can be used as the set of seed documents. In one embodiment, documents may be scanned using a scanner and processed with optical character recognition software.

The system and method may include gathering or being provided with a collection of source documents to be searched. For example, the source documents can be obtained or provided from the Internet or other sources, such as a database. The source of the documents may be static, meaning that no additional documents are added over time, or may be dynamic, meaning that documents may be added or deleted from the source over time. For example, source documents can be obtained from one or more Really Simple Syndication ("RSS") feeds. In one embodiment, the target documents include several thousand RSS feeds as the source. In one example, these entries were downloaded to a local computing machine and stored in a local database.

The content of the seed and source documents can vary from application to application. For example, seed documents can be related or unrelated to one another. That is, the seed documents may include a plurality of documents with disparate subject matter relative to one another, a plurality of documents with similar subject matter relative to one another, or a combination of some seed documents with disparate subject matter relative to other seed documents and some seed documents with similar subject matter relative to other seed documents. As another example, the source documents can be related to a certain topic, be derived from a particular source or set of sources, or be a random sampling of publicly available documents, for example, source documents available on the Internet or source documents available from a medical database.

Before or after generating a document vector, the documents may undergo processing. For example, in one embodiment, the system iterates through each of the seed and source documents, performing a number of steps, including the removal of stop words and the stemming of terms. Stop words are words that are common to a language. Stop words, such as "a, about, above, after . . . " are, themselves, known and are available in libraries. Stemming generally refers to the process of reducing inflected words to their base or root form, e.g., changing "tumors" to "tumor".

At this stage, the document may be automatically tagged using a parts of speech tagger to identify the syntax of a sentence, e.g., nouns, verbs, adverbs. Then, after processing, the document vector can be generated for each seed document.

Figure 1:
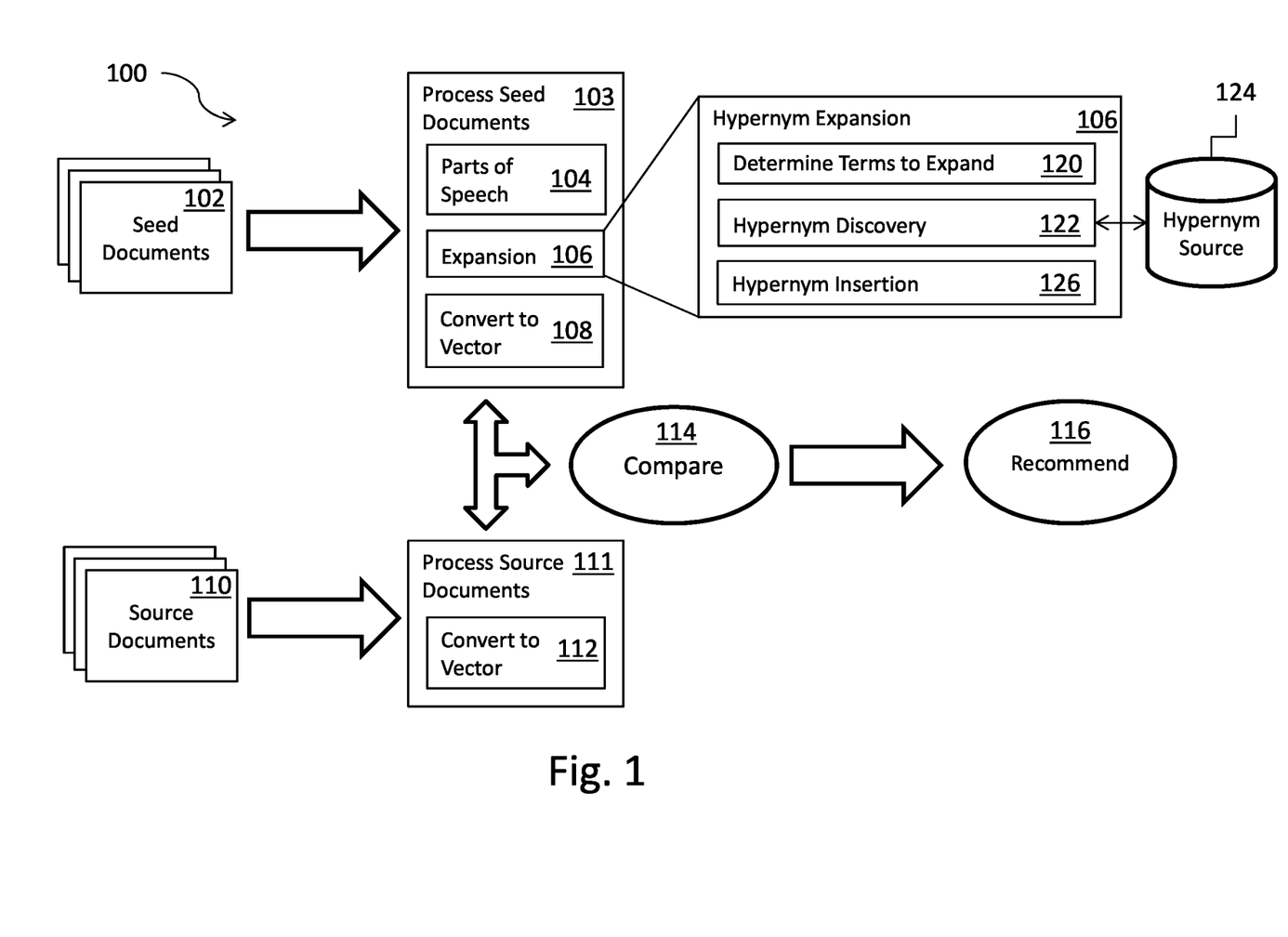
FIG. 1 is a flow diagram in accordance with an example system and method of the present invention.

An expansion 106 of the terms in each seed document can be conducted before or after each seed document is converted to a vector. The expansion 106 is a three-step process of: determining which terms in the seed document to expand; discovering one or more hypernyms (and/or hyponyms) for each of the terms to be expanded in each seed document; and inserting some or all of the discovered terms back into the respective seed document.

Determining Terms to Expand

It may be too time intensive or create too much noise conducting an expansion on every term in a seed document. There are a variety of different processes for determining which terms in the seed documents to expand 120. For example, in one embodiment, all of the non-stop words can be subject to expansion.

As another example, as shown in FIG. 1, a parts of speech analysis 104 can be utilized to narrow the candidate terms for expansion. The parts of speech analysis may be conducted in order to select terms that form a particular part of speech. Part of speech analysis can be used to determine which terms in each seed document are nouns, for example. Parts of speech analysis is well known and therefore will not be discussed in detail, suffice it to say, a document can be input to a parts of speech analysis software package and the various terms in the document can be labeled according to their part of speech, i.e., noun, adjective, verb, etc. In one embodiment, the nouns of each seed document can be identified for use in connection with the expansion. In alternative embodiments, different types of parts of speech can be labeled and used in processing the source and/or seed documents.

Alternatively or in addition to using the parts of speech analysis, the terms chosen to be the subject of the hypernym expansion may be based on the frequency of the term in the document. For example, a given document may have thousands of individual terms and in order to increase performance only a certain number or certain percentage are designated to be expanded. That is, a threshold frequency value or percentage of the most frequently occurring terms of the document may be selected for expansion. This may be combined with other methods of determining which terms to expand. For example, in one embodiment, the top 10% most frequently used nouns in each seed document may be selected for hypernym expansion.

Hypernym Discovery

Hypernym discovery 122 is the process by which a hypernym or set of hypernyms is identified for a given term. Hypernym discovery includes accessing a local or remote hypernym source 124. A hypernym source is a database, or other structure, that stores hypernymic relationships between terms. Depending on the source, an application programming interface (API), or another interface, may be provided that allows a user to input a term and receive one or more hypernyms of the term as output. In some embodiments, a hypernym source may be selectable by a user from several available hypernym sources. For example, a user may choose to use a medical hypernym database that is specifically tailored with relationships relating to medical terms instead of a generic hypernym source.

There are a variety of hypernym sources available that provide terms and set forth their hypernym relationship with other terms. For example, WordNet® is a large lexical database of nouns, verbs, adjectives and adverbs grouped into sets of cognitive synonyms. Many of the terms in WordNet® are encoded with hypernymy/hyponymy relationships, sometimes referred to as super-subordinate relationships or ISA relationships. The database links general terms such as "furniture" to increasingly specific ones like "bed" and "bunkbed." The WordNet® database is accessible online. See Princeton University "About WordNet", WordNet, Princeton University, 2010, <http://wordnet.princeton.edu>.

In one embodiment, hypernym discovery includes finding the first hypernym for each term being expanded, e.g., each noun, using a hypernym source, e.g., the WordNet® lexical database.

There are a large number of parameters that can be configured in connection with the hypernym discovery that can affect the results and the ultimate hypernym expansion. For example, the hypernym discovery process may obtain multiple hypernyms for each term. In addition, the hypernym discovery process may use filters to filter the hypernyms provided during the hypernym discovery process in a variety of ways.

A given term may have multiple hypernyms. Depending on the hypernym source, these hypernyms may be ranked or sorted based on one or more criteria. Accordingly, hypernym discovery may include providing all of the direct hypernyms, or alternatively, if the hypernym source provides one or more criteria for ranking the hypernyms, the hypernym discovery process may provide a subset of a given term's hypernyms based on the one or more criteria ordering the hypernyms.

Hypernym discovery may also include providing higher order hypernyms. For example, each hypernym may itself have a hypernym. The hypernym discovery process may be such that the hypernym source returns all (or a subset of) hypernyms a certain number of hops away from the term being expanded. For example, the term "lesion" may have a hypernym "tumor" which, in turn has a hypernym "growth", which in turn has a hypernym "illness." In this situation, the term "tumor" is a first order hypernym of, or one hop from, the term "lesion", the term "growth" is a second order hypernym of, or two hops from, the term "lesion", and the term "illness" is a third order hypernym of, or three hops from, the term "lesion."

Figure 3:
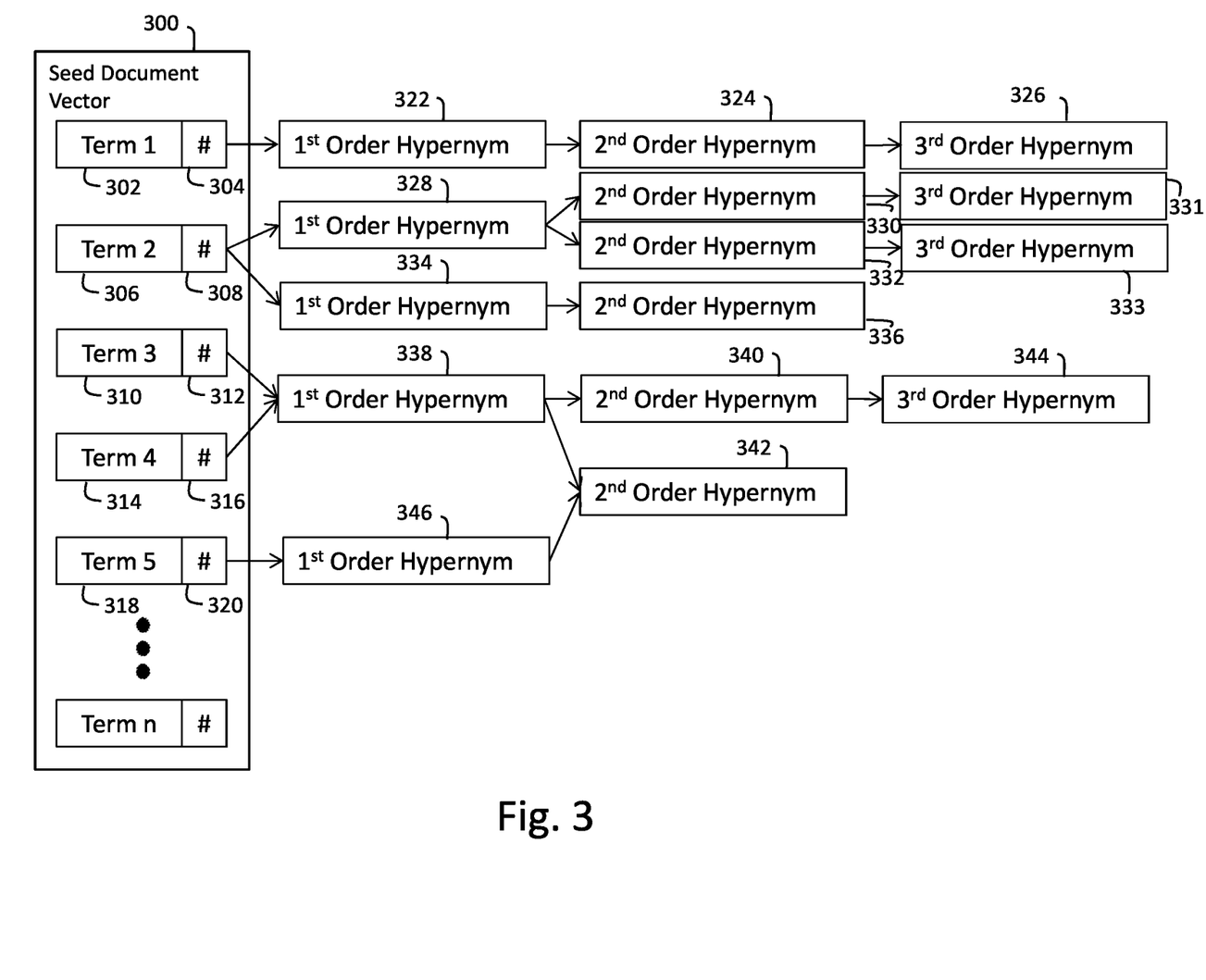
FIG. 3 illustrates an example seed document vector along with first, second, and third order hypernym relationships for five of the terms in the seed document vector.

FIG. 3 illustrates an example seed document vector 300 and hypernym relationships for five of the terms of the seed document vector. Each of the five terms 302, 306, 310, 314, and 318 are represented in the seed document vector. Adjacent to each term there is a numerical weight value 304, 308, 312, 316, 320 assigned during the term frequency process. In this example, hypernym discovery for terms 1-5 has provided the following hypernyms. Term 1 302 has three hypernyms: a first order hypernym 322, a second order hypernym 324, and a third order hypernym 326. Term 2 306 has seven hypernyms: two first order hypernyms 328, 334, three second order hypernyms 330, 332, 336, and two third order hypernyms 331, 333. Term 3 310 and term 4 314 share the same first order hypernym 338, and therefore share the same second and third order hypernyms 340, 342, 344. Term 5 318 has one first order hypernym 346, which shares a hypernym with the first order hypernym of term 3 and term 4 338. Accordingly, terms 3, 4, and 5 share a second order hypernym.

A variety of filters may also be provided in connection with the hypernym discovery process. For example, a predicate filter may be combined with the hypernym discovery such that a term is only returned if it not only has an "is a" hypernym relationship but also has an additional relationship, such as: coexists with, interacts with, does not interact with, affects, causes, or complicates, to list a few possible predicate filters. Context filters may also be utilized to remove non-context terms from the hypernym discovery process. The filters can be applied using any sort of Boolean or other logic operators.

Although the above description is given with respect to hypernym expansion, it should be understood that the same applies to other types of semantic relationship expansion, such as hyponym expansion. That is, the same parameters can be configured in connection with a hyponym discovery process. Further, in some embodiments, both hyponyms and hypernyms may be discovered as part of the discovery process.

Hypernym Insertion

Hypernym insertion 126 refers to the process of adding terms to a seed document or seed document vector that are hypernyms of other terms in that seed document. The inclusion of these additional terms increases the accuracy of the source document recommendation because certain source documents that are interesting documents desired by the user may not be recommended but for the increase in mathematical similarity between those documents due to the hypernym insertion. For example, by adding a more general version of a term to a seed document, source documents that utilize that term, but not the more specific term from the original seed document, can be recommended.

Hypernym insertion, to some extent, is limited by the previous steps of the hypernym expansion because only hypernyms that are discovered during the hypernym discovery process can be inserted into their respective seed documents. For example, if the discovery process is limited to only collecting first-order hypernyms for the five most frequently used terms in each seed document, it may be appropriate to insert all of the discovered hypernyms into their respective seed documents/vectors. In contrast, if the discovery process includes collecting all first, second, and third order hypernyms for every word in every seed document, then inserting all of the hypernyms may negatively impact performance, due to creation of noise and/or increasing processing time.

A balance can be struck during hypernym insertion. Inserting too many hypernyms into each seed document may create noise and decrease the accuracy of the process. However, inserting too few hypernyms into each seed document may not have a meaningful impact on the recommendation. Accordingly, to some extent, the amount of hypernyms inserted into each seed document may vary depending on a variety of factors that may be selectable by the user, or selected by the particular embodiment of the system. For this reason, the hypernym expansion 106 process may be performed iteratively with a user selecting different hypernym expansion criteria (e.g., different parameters for determining which terms to expand, hypernym discovery, and/or hypernym insertion) in order to search for interesting source document recommendations.

One approach to balancing the number of hypernym insertions is to place a threshold limit on the number of hypernyms inserted into each seed document/vector. For example, referring to FIG. 3, if the limit were a simple static limit of six hypernyms per term, then: all of the hypernyms for terms 1, 3, 4, and 5 would be inserted into the seed document vector, but only six of the seven hypernyms of term 2 would be inserted into the seed document. Essentially any criteria can be utilized to determine which six of the seven hypernyms are inserted. Generally, in many embodiments, lower order hypernyms will be given preference over higher order hypernyms. If the limit would cause some, but not all hypernyms of a certain order to be inserted, the process may either use a pre-defined or selected criteria to decide which hypernym to insert, or alternatively may insert all or none of the hypernyms of that order.

Another approach to balancing the number of hypernym insertions is to insert hypernyms shared by multiple terms in the seed document. For example, terms 3 and 4 share hypernyms 338, 340, 342, and 344 and terms 3, 4, and 5 share hypernym 342. By limiting the hypernym insertion to shared hypernyms, the accuracy of the document recommendations can be increased.

This shared hypernym approach can be modified in a variety of different ways. In some embodiments, only shared hypernyms of a certain order or lower are inserted. For example, in one embodiment, shared first and second order hypernyms are inserted, but third and later order shared hypernyms are not. In another embodiment, only hypernyms shared by a certain number of terms are inserted. For example, in one embodiment, only hypernyms shared by three terms are inserted. Applying this to the FIG. 3 example, only hypernym 342 would be inserted. In some embodiments, only the hypernym that is directly shared by two hypernyms is inserted. In FIG. 3, this would mean hypernyms 338, 342 would be inserted, but hypernyms 346, 340, and 344 would not be inserted.

Hypernym insertion may include not only deciding which hypernyms to insert into the seed documents, but also determining the frequency or weight associated with each inserted hypernym. If a hypernym is inserted before vectorization, then the term can be inserted in the seed document multiple times in order to achieve the desired frequency. If a hypernym is inserted after vectorization is complete, then the term can be inserted into the seed document vector along with a selected weight. In some embodiments, the term may be inserted during the vectorization process after the frequency information has been collected so that the hypernym and the numeric frequency value can be inserted and the TF/ICF or TF/IDF process can determine the weights for each of the terms in the seed document. Perhaps in the simplest embodiment, a given hypernym is inserted at a direct one-to-one ratio into the seed document before it is vectorized such that each hypernym appears in the source document/vector at the same frequency as the base term used in discovering that hypernym.

Adjusting the frequency or weight of the hypernyms inserted into the seed document may be useful. That is, instead of declining to insert a hypernym into a seed document in order to reduce the risk of noise, the hypernym may still be inserted but at a lower frequency or weight in order to reduce its impact on the vector comparison. Further, the frequency or weight at which a hypernym is inserted can be increased in order to amplify its impact on the vector comparison.

The frequency or weight of the hypernym can be adjusted based on a variety of factors. For example, the frequency or weight of a hypernym being inserted into a seed document may be adjusted based on its hypernym order. First order hypernyms may be inserted at the same frequency or weight as the base term, while second order or higher order hypernyms may be inserted at a lesser or greater frequency or weight, depending on the desired effect on the recommendation. Further, in some embodiments, the frequency or weight of the hypernyms inserted into the seed document/vector may vary depending on the frequency or weight of the base term. For example, a term that appears more frequently or has a greater weight in the seed document/vector may have hypernyms inserted at a greater frequency or weight relative to terms that appear less frequently or have a lower weight in the seed document/vector.

Similarly, the frequency or weight of the inserted hypernyms can be adjusted based on whether the hypernym is derived from multiple terms in the seed document. For example, if the term "chair" appears 10 times in the source document and the term "recliner" appears 30 times, then the term "furniture" may be inserted into the document at a frequency of 40. This may result in a hypernym that has a meaningful impact on the vector similarity comparisons and ultimate recommendation. As another example, if 50 terms in a seed document all share the same hypernym, and each of those 50 terms occurs 10 times in the document, then by inserting that hypernym with a frequency of 500 may have a meaningful impact on the vector similarity comparisons and ultimate recommendation.

It should be understood that FIG. 3 is a relatively simplistic hypernym graph designed to aid the explanation of the various hypernym expansion processes and various parameters that can be adjusted. In practice, each seed document vector may include hundreds, thousands, or more terms. And, many of those terms may have multitudes of hypernyms, many of which are shared among the terms of the seed document.

Referring back to FIG. 1, the seed and source documents can be converted to vectors 108, 112. The seed documents can be converted to vectors 108 before or after the expansion 106.

Essentially any method for generating a document vector can be utilized. In the current embodiment, a document vector can be generated for a document using the Term Frequency/Inverse Corpus Frequency (TF/ICF) method, as disclosed in U.S. Pat. Nos. 7,693,903, 7,805,446, and 9,558,185, each of which were incorporated by reference above. In alternative embodiments a document vector can be generated using a different method.

In another embodiment, predetermined seed document vectors and source or target document vectors can be received. Generating document vectors may be unnecessary, for example, if they have already been generated previously. Document vectors, either seed document vectors or source document vectors, can be received by retrieving them from memory. For example, a database of document vectors may be available. The database may be available internally in memory of the computer handling the search or alternatively may be available externally in memory of a different system.

Some embodiments can include a combination of receiving predetermined document vectors and generating document vectors. For example, in some embodiments, predetermined source document vectors are received and seed document vectors are generated. In other embodiments, some source document vectors and/or seed document vectors are generated and some predetermined target document vectors and/or predetermined seed document vectors are received.

An additional processing step can be conducted to remove terms that are too significant such as disclosed in U.S. Pat. No. 9,256,649 to Potok et al. In one embodiment, the top n highest weighted terms, where n is supplied by the user or pre-defined in the system, can be extracted from the seed document vectors. This list can be used as a list of significant search terms.

For each of these terms, a search of a source document index is conducted that returns the number of documents that contains the term. If the number of documents returned is less than (x) percent of the total number of documents, then the term is kept, otherwise the term is removed from the seed documents. The source document index can be previously prepared and provided to the system or created by analyzing the source documents with automatic indexing software or other more sophisticated methods.

The similarity between a seed document and a source document can be ascertained by comparing the seed document vector and the source document vector. This can also be referred to as a search. Perhaps the comparison can be best understood in connection with FIG. 1, which illustrates a representative flow diagram 100.

Referring to FIG. 1, an embodiment that includes generating seed document vectors and source document vectors, the system retrieves source documents 110 and creates a source document vector 112 for each. The system also retrieves one or more seed documents 102 and for each creates a seed document vector 108 for that document. The seed document vector may be created from a seed document modified with a semantic relation expansion, such as hypernym expansion 106, or the expansion of terms may be conducted once the seed document is in vector form by adding additional term and frequency information to the vector based on the expansion 106. Each source document vector is then compared 114 to each seed document vector using a dot product, or other method of comparison, of the two vectors to represent the similarity of the terms within the two documents. The result can be recorded as a similarity tuple including <seed document name or ID>, <source document name or ID>, and <similarity>.

This process can be iterated to generate a similarity tuple for every combination of source document and seed document. For example, with three seed documents and 1,000 source documents, the process can generate 3,000 similarity tuples—one tuple for every combination of seed document and source document.

The order of the comparisons can vary. For example, the source document vector can be compared to each of the remaining seed document vectors, for example where there are ten seed documents there would be nine remaining seed documents, and the similarities tuples can be recorded for those comparisons. At that stage, one source document has been compared to all of the seed documents. Each of the remaining source documents may then be compared to each of the ten seed document vectors, and the similarities tuples can be recorded for each comparison. Now, all of the source documents have been compared to all of the seed documents, and the results recorded. In another embodiment, each seed document vector could be taken in turn and compared to every source document before moving to the next.

The results of the comparison can be sorted based on the similarity values. For example, in embodiments where similarity tuples are recorded, the similarity tuples can be sorted based on the similarity values from highest to lowest, so that the similarity tuple with the most similar seed and source documents are at the top of the list. This can simplify the review by the user or a piece of software of the most relevant document for each of the seed documents. In alternative embodiments, the results can be sorted differently. For example, the results can be sorted in reverse, from lowest similarity value to highest similarity value.

Recommendations of source documents can be made based on the similarity of the individual seed documents to the target documents as opposed to recommendations based on the similarity of a collection of seed documents to the target documents. That is, the individual seed document vectors and their similarity to the target documents can be preserved.

Recommendations based on the search can be provided to a user. For example, the system can recommend a certain source document that is similar to a certain seed document. In one embodiment, the recommendation can include displaying on a computer monitor a filtered list of sorted similarity tuples. For example, a list of unsorted similarity tuples can be sorted into a list of sorted similarity tuples from highest similarity value to lowest similarity value. The list of sorted similarity tuples can be formatted into a recommendation including a list of the three similarity tuples with the highest similarity values. The recommendation can be in the form <seed document name> recommends <source document name> at similarity <similarity>. Thus one of the seed documents can "recommend" a target document with an indication of the similarity ranking.

In alternative embodiments, the system can provide a recommendation by filtering or otherwise organizing the results differently in order to identify interesting source documents that are similar to a seed document. For example, the results can be filtered to provide a certain number of the highest similarity tuples for each seed document, instead of a certain number of the highest similarity tuples regardless of the originating seed document.

The recommendation or output can be produced in a variety of different formats. For example, the output can be produced in XML format so that an RSS Reader can format the XML. This can allow for easy Internet access to the recommendations. As another example, the recommendation can be provided in a text file.

Figure 2:
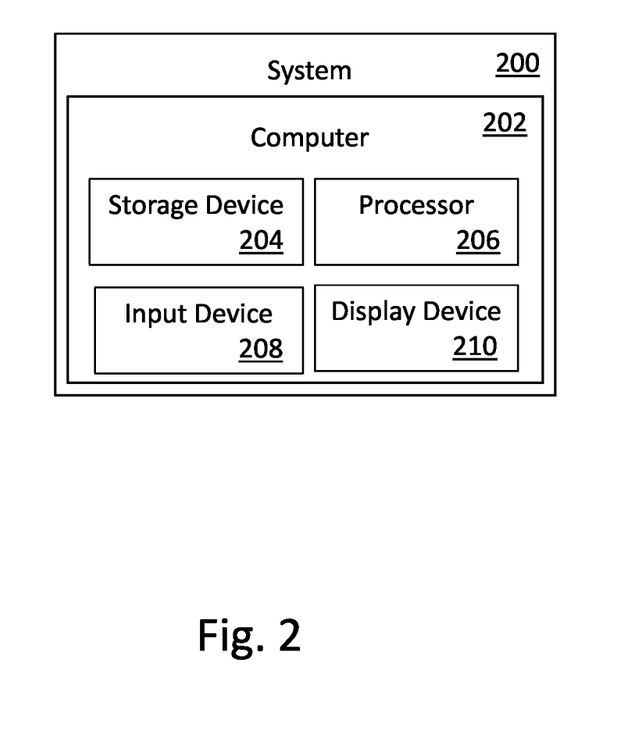
FIG. 2 is a system diagram in accordance with an example system and method of the present invention.

One embodiment of a system 200 that implements the method described above for recommending documents using hypernym expansion is illustrated in FIG. 2. Referring to FIG. 2, a computer apparatus 202 is part of a system 200 used to execute a series of commands representing the method steps described above. The computer 202 may be a mainframe, a super computer, a PC or Apple Mac personal computer, a hand-held device, a smart phone, or another central processing unit known in the art. The computer 202 is programmed with a series of instructions that, when executed, cause the computer 202 to perform the method steps as described and claimed in this application. The instructions that are performed are stored on a machine-readable data storage device 204. In the illustrated embodiment, the computer 202 includes a processor 206, input device 208, and a display device 210.

The machine-readable data storage device can be a portable memory device that is readable by the computer apparatus. Such portable memory device can be a compact disk (CD), digital video disk (DVD), a Flash Drive, any other disk readable by a disk driver embedded or externally connected to a computer, a memory stick, or any other portable storage medium currently available or yet to be invented. Alternately, the machine-readable data storage device can be an embedded component of a computer such as a hard disk or a flash drive of a computer.

The computer and machine-readable data storage device can be a standalone device or a device that is imbedded into a machine or system that uses the instructions for a useful result. The computer may be part of a larger system or network of connected computers.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

While this disclosure describes and enables several examples of a system and method for recommending and discovering interesting documents, other examples and applications are contemplated. Accordingly, the invention is intended to embrace those alternatives, modifications, equivalents, and variations as fall within the broad scope of the appended claims. The technology disclosed and claimed herein is available for licensing in specific fields of use by the assignee of record.

The embodiments of the invention in which an exclusive property or privilege is claimed are defined as follows:

1. A method for recommending interesting documents using a computer, the method comprising:
   obtaining a seed document vector for each of a plurality of seed documents, each seed document vector having a seed document identifier, a plurality of terms, and a plurality of corresponding term weights;
   obtaining a source document vector for each of a plurality of source documents, each source document vector having a source document identifier, a plurality of terms, and a plurality of corresponding term weights;
   determining a set of first-order hypernyms for each respective seed document vector based on the plurality of terms of the respective seed document vector, wherein each hypernym in the set of first-order hypernyms is a hypernym of at least one of the plurality of terms in the respective seed document vector and at least two different terms in the respective seed document vector share at least one hypernym in the set of first-order hypernyms;
   determining a set of second-order hypernyms for each respective seed document vector based on the determined set of first-order hypernyms of the respective seed document vector, wherein each hypernym in the set of second-order hypernyms is a hypernym of at least one of the hypernyms of the set of first-order hypernyms of the respective seed document vector;
   associating with each respective seed document vector, using a processor, one or more hypernyms from the set of first-order hypernyms and the set of second-order hypernyms as additional terms of each respective seed document vector;
   associating with each respective seed document vector, using the processor, a corresponding weight for each of the one or more hypernyms of the set of first-order hypernyms and the set of second-order hypernyms associated with each respective seed document vector, wherein the corresponding weight for each of the one or more hypernyms is based, at least in part, on whether the hypernym is in the set of first-order hypernyms or the set of second-order hypernyms, how many different terms of the plurality of terms in the respective seed document vector share the hypernym in the set of first-order hypernyms or the set of second-order hypernyms, respectively, and corresponding weights of the different terms that share the hypernym;
   comparing, using the processor, each source document vector to each seed document vector to obtain a similarity value for each comparison; and
   recommending, using a display device, one or more of the plurality of source documents based on respective similarity values.

2. The method of claim 1 including determining a set of terms from one or more of the plurality of seed documents to expand by hypernym expansion.

3. The method of claim 2 including conducting a parts of speech analysis on one or more of the plurality of seed documents, wherein determining the set of terms from one or more of the plurality of seed documents to expand by hypernym expansion includes selecting terms that form a particular part of speech identified during the parts of speech analysis.

4. The method of claim 2 including obtaining one or more hypernyms for each term in the set of terms from one or more of the plurality of seed documents from a hypernym source.

5. The method of claim 4 wherein obtaining one or more hypernyms for each term in the set of terms includes selecting one or more hypernyms based on at least one of a user selected criteria and a pre-defined criteria.

6. The method of claim 4 wherein obtaining one or more hypernyms for each term in the set of terms includes selecting one or more hypernyms based on at least one of a user selected filter and a pre-defined filter.

7. The method of claim 1 including limiting the associating of hypernyms with each respective seed document vector to only hypernyms shared by at least three different terms in each respective seed document vector.

8. The method of claim 1 including limiting the associating of hypernyms with each respective seed document vector to only hypernyms shared by multiple different terms in each respective seed document vector.

9. A method for discovering documents using a computer and bringing them to the attention of a human observer, the computer being programmed with a series of instructions that, when executed, cause the computer to perform the method steps comprising:
   defining one or more seed documents of interest;
   processing each seed document by removing stop words and stemming terms;

generating a seed document vector for each seed document, wherein the seed document vector includes a plurality of terms and corresponding weights;
receiving a plurality of source documents and generating a source document vector for each source document;
determining a set of hypernyms for each respective seed document vector, wherein the set of hypernyms is based on the plurality of terms of the respective seed document vector and includes hypernyms of different orders, wherein hypernyms of different orders include first-order hypernyms derived from one or more of the plurality of terms in the respective seed document vector and second-order hypernyms derived from one or more of the first-order hypernyms, wherein each hypernym of the first-order hypernyms is a hypernym of at least one of the plurality of terms in the respective seed document vector and at least two different terms in the respective seed document vector share at least one hypernym of the first-order hypernyms;
associating each set of hypernyms with each respective seed document vector as one or more additional terms of the respective seed document vector;
determining a corresponding weight for each hypernym in each set of hypernyms, wherein the corresponding weight for each hypernym is based, at least in part, on whether the hypernym is a first-order hypernym or a second-order hypernym, how many different terms of the plurality of terms in the respective seed document vector share the hypernym as a first-order hypernym or a second-order hypernym, respectively, and corresponding weights of the different terms that share the hypernym;
associating the corresponding weight for each hypernym in each set of hypernyms with the additional terms of each respective seed document vector;
comparing each of the source document vectors to each of the seed document vectors using a dot product of the two vectors to represent the similarity of the terms within the seed document vector and the source document vector to obtain a document similarity value for each comparison; and
generating and displaying, using a display device, a recommendation of one or more source documents based on the document similarity values obtained by comparing the source document vector to the seed document vector.

10. The method of claim 9 including selecting a set of terms from each seed document to expand by hypernym expansion.

11. The method of claim 10 including conducting a parts of speech analysis on each seed document and wherein selecting the set of terms from each seed document to expand by hypernym expansion includes selecting terms that form a particular part of speech identified during the parts of speech analysis.

12. The method of claim 10 including obtaining one or more hypernyms for each term in the set of terms from the seed document from a hypernym source.

13. The method of claim 12 wherein obtaining one or more hypernyms for each of the terms includes selecting one or more hypernyms based on at least one of a user selected filter and a pre-defined filter.

14. The method of claim 9 including limiting the determined set of hypernyms for each respective seed document vector to hypernyms shared by multiple different terms in each respective seed document vector.

15. The method of claim 9 including limiting the determined set of hypernyms for each respective seed document vector to only hypernyms shared by at least three different terms in each respective seed document vector.

16. A system for discovering documents for a human observer, the system comprising:
a computer having a storage device, a processor, and an input device for obtaining a plurality of seed document vectors corresponding to a plurality of seed documents and obtaining a plurality of source document vectors corresponding to a plurality of source documents, and a display device; and
wherein the processor performs a method comprising:
determining a set of first-order hypernyms for at least one seed document of the plurality of seed documents based on content of the at least one seed document, wherein each hypernym in the set of first-order hypernyms is a hypernym of at least one of a plurality of terms in the at least one seed document such that at least two different terms in the at least one seed document share at least one hypernym in the set of first-order hypernyms;
determining a set of higher-order hypernyms for the at least one seed document based on the determined set of first-order hypernyms, wherein each hypernym in the set of higher-order hypernyms is a hypernym ultimately derived from at least one of the hypernyms of the set of first-order hypernyms;
associating at least one first-order hypernym from the determined set of first-order hypernyms and at least one higher-order order hypernym from the determined set of higher-order hypernyms with a respective seed document vector of the plurality of seed document vectors corresponding to the at least one seed document of the plurality of seed documents;
determining a corresponding weight for each of the first-order hypernyms and each of the higher-order hypernyms, wherein the corresponding weight is based, at least in part, on whether the hypernym is a first-order hypernym or a higher-order hypernym, how many different terms of the plurality of terms in the respective seed document vector that share the hypernym as a first-order hypernym or a second-order hypernym, respectively, and corresponding weights of the different terms that share the hypernym;
associating the corresponding weight with each respective seed document vector;
comparing each of the plurality of source document vectors to each of the plurality of the seed document vectors to obtain a similarity value; and
wherein the display device displays a recommendation of one or more source documents for the human observer on the display device based on the document similarity value.

17. The system of claim 16 including selecting a set of terms from each of the plurality of seed documents to expand by hypernym expansion and conducting a parts of speech analysis on each of the plurality of seed documents, wherein selecting the set of terms from each seed document to expand by hypernym expansion includes selecting terms that form a particular part of speech identified during the parts of speech analysis.

18. The system of claim 16 including associating a plurality of hypernyms from the set of first-order hypernyms and the set of higher-order hypernyms with the at least one respective seed document vector, and limiting the association to only hypernyms shared by multiple different terms in the at least one respective seed document vector.

19. The system of claim 16 including limiting the association to only hypernyms shared by at least three different terms in the at least one respective seed document vector.

* * * * *